United States Patent [19]

Pellegrino et al.

[11] Patent Number: 5,311,567

[45] Date of Patent: May 10, 1994

[54] IDENTIFICATION FLASHER X-RAY FILM LABELING UNIT

[75] Inventors: Anthony J. Pellegrino, New Fairfield; Robert H. Brady, Brookfield; David D. Camarra, Fairfield, all of Conn.

[73] Assignee: Lorad Corporation, Danbury, Conn.

[21] Appl. No.: 27,577

[22] Filed: Mar. 5, 1993

Related U.S. Application Data

[63] Continuation of Ser. No. 795,820, Nov. 21, 1991, abandoned.

[51] Int. Cl.$^5$ .............................................. H05G 1/28
[52] U.S. Cl. ...................................... 378/166; 378/162
[58] Field of Search ............................ 378/165, 166

[56] References Cited

U.S. PATENT DOCUMENTS 3,973,130  8/1976  Amemiya ........................... 378/166
4,520,497  5/1985  Kluge et al. ........................ 378/166

Primary Examiner—Craig E. Church
Attorney, Agent, or Firm—Ware, Fressola, Van Der Sluys & Adolphson

[57] ABSTRACT

An identification labeling unit for applying identifying data to a sheet of X-ray film enclosed in a film cassette has data input means and a cassette insertion slot extending into the interior of its housing; a data display device, such as a vacuum fluorescent data display screen, defines an object plane inside the housing, and an optical system delivers an image of the data display screen focussed at an image plane within the cavity slot. When the X-ray film-enclosing cassette is fully inserted into the insertion slot, with a corner window hatchcover on the cassette being automatically opened by the cassette's insertion into the cavity slot, the corner of the X-ray film receives the focussed labeling data image from the optical system.

4 Claims, 2 Drawing Sheets

IDENTIFICATION FLASHER X-RAY FILM LABELING UNIT

This is a continuation of Ser. No. 795,820 filed Nov. 21, 1991 and now abandoned.

FIELD OF THE INVENTION

This invention relates to devices for labeling X-ray films with the date, the anatomical site, the patient's and physician's identifying data, and more particularly to automatic units deriving information from a microcomputer controlled X-ray machine and also from a computer having a data input keyboard associated with the automatic labeling unit.

RELATED ART

Conventional labeling systems marketed by Kodak or by Agfa-Gevaert for identification of X-ray films generally involve typewriting or hand-lettering with special metallic suspension X-ray opaque inks on gummed labels or cards applied to or imaged on the unexposed X-ray film, or to X-ray transparent film holders or cassettes. The labor time required to prepare and apply such labels or cards is considerable, but is often necessary because accurate permanent labels are required, preferably as part of the recorded X-ray image itself, in order for the radiologist to make effective use of the X-ray in current diagnosis and for medical history purposes.

Conventional labeling units cooperate with an X-ray film cassette having a normally closed sliding hatchcover overlying one corner of the enclosed X-ray film. The labeling unit is enclosed in a light-tight housing provided with a cassette-receiving insertion cavity slot shaded from external illumination, into which the labeling "window" corner of the cassette is slidingly inserted.

One conventional labeling device, the Kodak Diagnostic Imaging Portable Identification Camera, described in Kodak Publication Part No. 635,924 of August, 1989, accommodates any of three different Kodak X-ray film cassettes. It employs a pivoted, rocking cassette hatch-cover actuator which engages a recess in the hatchcover and draws it open as the cassette is inserted into the insertion slot along a guide edge to expose a window hatchway. A patient data card imprinted with information is inserted in a card slot, and the data thereon is illuminated briefly by a pair of lamp bulbs and projected onto the X-ray film through the open window hatchway, after which withdrawal of the cassette from the insertion slot automatically closes the hatchcover.

SUMMARY OF THE INVENTION

In the devices of the present invention, the advancing cassette engages a hatch retractor serving to slide the hatchcover open, presenting the underlying corner of the X-ray film on the focal plane of a labeling optical system. This system displays all desired alphanumeric or graphical labeling data as a focussed image of a vacuum fluorescent display or other light emitting display, labeling the exposed film in the cassette. One or more data input keyboards supply the data displayed on the vacuum fluorescent display, and a convenient external display screen is also provided, eliminating the need for hand lettering or typing of cards, or application of adhesive labels.

Accordingly, a principal object of the invention is to provide an X-ray film labeling unit capable of rapid, accurate, automatic labeling of the film inside a cassette with all desired relevant identifying data.

Another object is to provide such an X-ray film labeling unit with an input keyboard for entry of data just prior to the film labeling operation.

Still another object is to provide such an X-ray film labeling unit capable of combining data received from the X-ray projection system with data from other input sources.

A further object is to provide such an X-ray film labeling unit incorporating a high contrast vacuum fluorescent display or "VFD" module, producing a sharp clear labeling image focused by an internal optical system on the X-ray film itself.

Other objects of the invention will in part be obvious and will in part appear hereinafter.

The invention accordingly comprises the features of construction, combination of elements, and arrangement of parts which will be exemplified in the construction hereinafter set forth, and the scope of the invention will be indicated in the claims.

THE DRAWINGS

For a fuller understanding of the nature and objects of the invention, reference should be made to the following detailed description taken in connection with the accompanying drawings, in which.

BEST MODE FOR CARRYING OUT THE INVENTION

Figure 1:
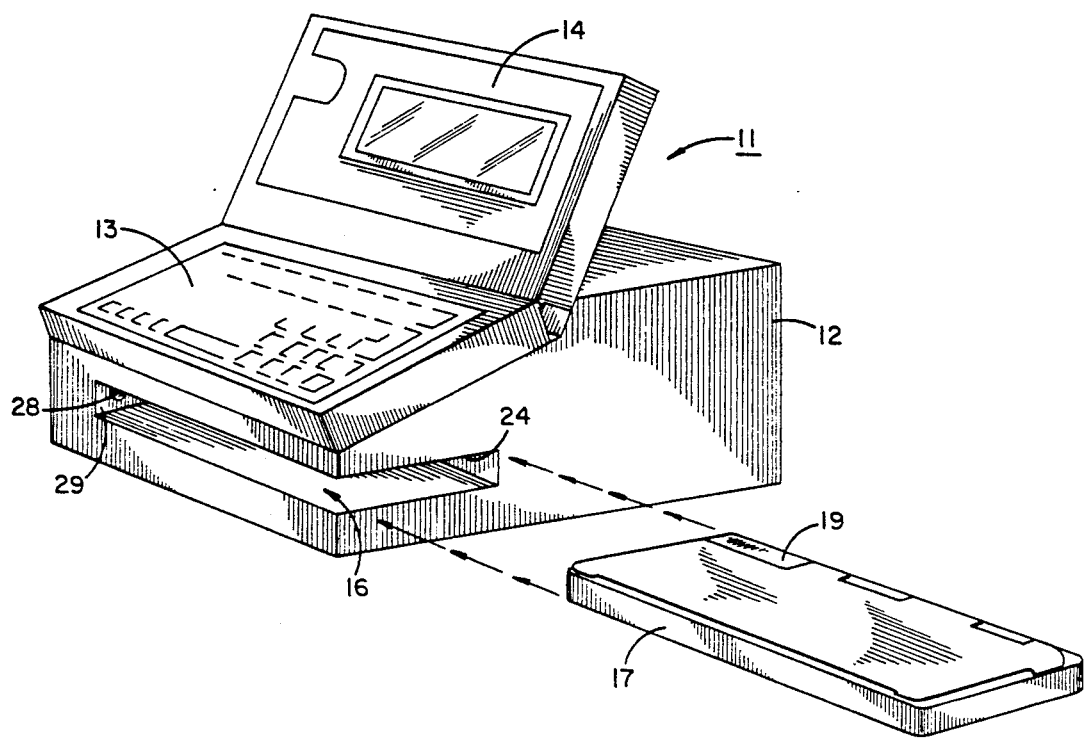
FIG. 1 is a schematic perspective view of the X-ray film cassette labeling unit characterizing the invention, showing a film cassette in the process of being inserted into the unit for labeling.
Figure 2:
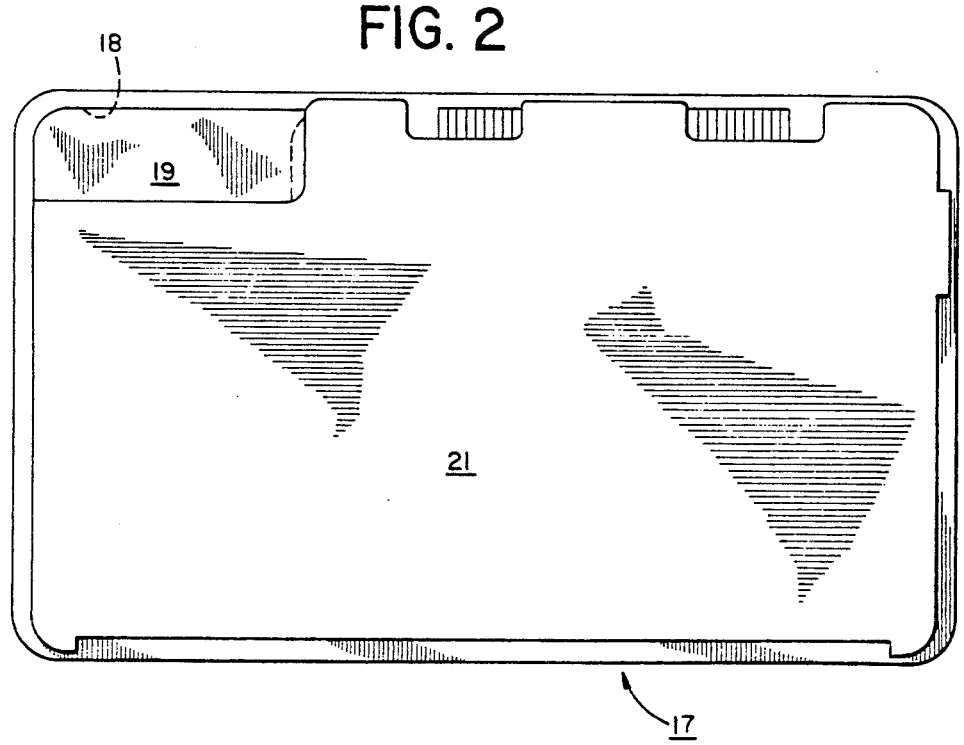
FIG. 2 is a top plan view of an X-ray film cassette, showing the sliding hatch closed, to be automatically opened for labeling by the labeling unit.

The X-ray film labeling unit of the present invention is accessed by the user at a cassette labeling unit 11. As shown in the drawings, and particularly in FIG. 1, unit 11 is preferably enclosed in a small light-tight desktop housing 12, surmounted by a miniature data entry keyboard 13 and an external data display screen 14, both cooperating with computer 15, which may all be found combined in such economical commercial products as the ATARI® Portfolio ™ "palmtop" computer, or the larger COMPAQ® LTE® "notebook" computers.

Keyboard 13, mounted slanting on the upper front of housing 12, provides easy access for data entry by the user, while hinged fliptop display screen 14 can be stored in its down-folded position atop keyboard 13 (FIG. 3), and swung upward to its deployed display position (FIG. 1) by the user whenever desired.

As shown in FIG. 1, housing 12 is provided with a horizontal insertion cavity slot 16 opening outward to the front and to the right side, at its right front corner. Slot 16 is generally rectangular in plan, and is dimensioned for freely sliding insertion of the corner window portion of an X-ray film cassette 17. A labeling window hatchway 18, closed by a sliding hatchcover 19, is formed in the upper left corner of the upper face 21 of cassette 17. As shown in FIG. 1, when cassette 17 is presented face up for right-to-left sliding insertion into slot 16, the hatchcover 19 is positioned in the left rear or distal portion of cassette 17, and the window hatchway 18 automatically slides into the innermost rear corner of slot 16, where the overlying ceiling surface portion 24 of housing 12 blocks ambient light from reaching that corner of the cassette.

Right-to-left sliding insertion of cassette 17 into slot 16 brings sliding hatchcover 19 into interfering engagement with a conventional spring biased retractor actuator, automatically sliding the hatchcover open. Ensuing leftward movement of cassette 17, from its FIG. 4 position toward its FIG. 5 position, causes cassette 17 to move into seated engagement against a limit switch 28 positioned in the left end wall 29 of slot 16, while hatchcover 19 is held open by the actuator, thereby opening window hatchway 18 and leaving the underlying corner of X-ray film 31 presented via an image delivery portal 20 to the interior of housing 12 for the imaging of labeling data thereon.

After labeling, left-to-right retraction of cassette 17 from slot 16 causes the actuator to draw hatchcover 19 leftward relative to hatchway 18. When cover 19 has closed hatchway 18, the actuator is cammingly disengaged by further rightward movement of cassette 17, thereby completing the labeling of the film 31 enclosed in the cassette.

Exposure of X-ray Film to Labeling Image

Figure 4:
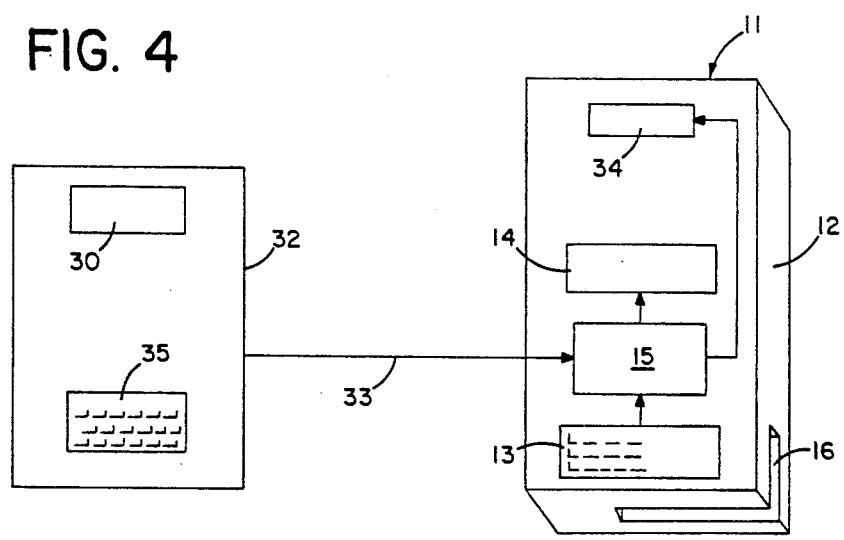
FIG. 4 is a schematic block circuit diagram of the labeling unit of the invention.

As shown schematically in FIG. 4, the X-ray machine 32, which can have its own microcomputer with a display 30 and input means, such as data entry keyboard 35, touchscreen, mouse or the like, is preferably connected to labeling unit housing 12 by a data line 33 via the buffer memory of computer 15 associated with keyboard 13, and data concerning time and intensity of the exposure or other variables from data line 33 can thus be used alone, or combined with any keyboard data entered on labeling unit keyboard 13, to provide the completed labeling data displayed for checking on external screen 14.

Figure 3:
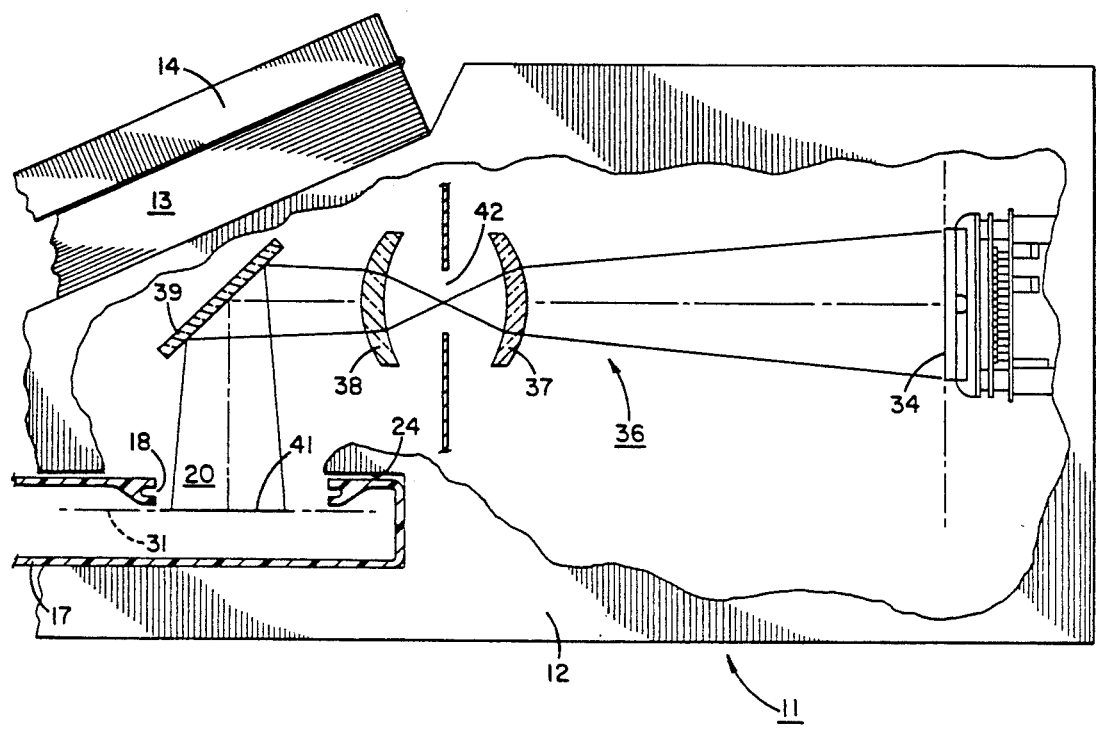
FIG. 3 is an enlarged schematic side elevation view, partially broken away, showing the optical system employed in the labeling unit.

The data display circuitry of labeling unit 11 delivers the labeling data to a vacuum fluorescent display or VFD module 34 mounted facing forward near the back wall of housing 12, as shown in FIG. 3. The Noritake model GUR256x64-312 VFD provides a suitable display configuration for this purpose, capable of displaying eight lines of thirty-two characters each, and preferably employed to display six lines of characters combined with a graphic display identifying the exposure angle or the like.

A folded optical system 36 (FIG. 3) has the internal VFD display area 34 at its object plane, and a pair of meniscus lenses 37, 38 focus this display, after one reflection from mirror 39, onto an image plane 41 coinciding with the surface of X-ray film 31 which is presented via portal 20 through the open hatchway 18 under the inmost corner of ceiling 24 in cavity slot 16.

In one embodiment, the total length along the optical axis from object plane 34 through lenses 37 and 38 and mirror 39 to image plane 41 is 271.42 mm. Lenses 37 and 38 are both f102.40 mm, flanking a central aperture 42 just under 8.0 mm wide, minimizing aberration or distortion, and which is 167.0 mm from VFD object plane 34, and 104.4 mm from image plane 41. The aperture of approximately 8 mm width allows a typical exposure time of 1/10 sec., but the exposure time is user variable and is set to produce a good image based on the film type and film processing system. The display circuitry energizes the VFD display for the desired short period of time, creating a brief "flash" display imaged at image plane 41 on the X-ray film 31 through portal 20 and open window hatchway 18.

The remaining area of film 31 is not exposed to this labeling image, which therefore does not affect the previous or subsequent X-ray exposure of the film 31 in cassette 17 for the patient's radiography.

The flasher film labeling unit of this invention thus provides simplified data collection and entry, derived from the X-ray machine itself, from the keyboard 13 mounted on the labeling unit 11 and from any other desired sources, additional keyboards or the like. Facile editing and checking is also provided on the external display screen 14 adjacent to keyboard 13. Extra cards or labels are totally eliminated, and the X-ray film labeling operation is readily and quickly expedited by the devices of this invention.

It will thus be seen that the objects set forth above, and those made apparent from the preceding description, are efficiently attained and, since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An identification labeling assembly, for association with an x-ray machine, responsive to an input control signal provided in response to an operator input, for providing identifying labeling data for recordal on a sheet of x-ray film enclosed in a film cassette having a corner window hatchway with a sliding hatchcover, said assembly comprising:

A. a housing incorporating a single cassette insertion slot with hatchcover opening and closing means therein, said housing having otherwise a totally closed outer surface unbroken by card insertion slots, B. external data input means, responsive to data input by said operator, for providing a first data input control signal, C. computer means, responsive to said first data input control signal and to a second data input control signal from the x-ray machine for providing first and second display signals for displaying data for recordation, D. external data display means, responsive to said first and second display signals for displaying said data for recordation, wherein said external data input means, said computer means and said external data display means together form a portable computer unit, mounted on said housing, E. means forming a self-illuminated internal display screen defining an object plane positioned inside said housing, substantially isolated from external illumination, and responsive to said first and second display signals from said computer means for displaying said data for recordation on said object plane display screen, F. an optical system positioned inside said housing and aligned to provide an image solely of said object plane focussed at an image plane within said cassette-insertion slot, avoiding said need for insertion slots to receive data-bearing cards or labels as objects to be imaged for labeling said film, and G. trigger means connected to energize said internal display screen for automatically providing said data for recordation via said optical system to said image plane when said cassette is inserted in the insertion slot and the window hatchway is opened and when said cassette contacts said trigger means, whereby the sheet of x-ray film has said data for recordation applied to it photographically without requiring separate typewritten or handwritten data cards or labels.

2. The labeling assembly defined in claim 1 wherein the self-illuminated internal display screen inside the housing is a vacuum fluorescent display device.

3. The labeling assembly defined in claim 1, wherein the external data input means is a first input keyboard mounted on the housing.

4. The labeling assembly defined in claim 1, wherein the external data display means is a display screen adjacent to the external data input means.

* * * * *